United States Patent
Pichler et al.

(10) Patent No.: US 8,583,575 B2
(45) Date of Patent: Nov. 12, 2013

(54) PROCESS AND DEVICE FOR REPRESENTATION OF A SCANNING FUNCTION

(75) Inventors: Alexander Pichler, Altkirch (FR);
Pierre Raymond, Heimsbrunn (FR);
Marc Eichhorn, Mannheim (DE)

(73) Assignee: Institut Franco-Allemand de Recherches de Saint-Louis, Saint-Louis (FR)

( * ) Notice: Subject to any disclaimer, the term of this patent is extended or adjusted under 35 U.S.C. 154(b) by 518 days.

(21) Appl. No.: 12/801,625

(22) Filed: Jun. 17, 2010

(65) Prior Publication Data

US 2011/0055129 A1     Mar. 3, 2011

(30) Foreign Application Priority Data

Jun. 24, 2009    (DE) .......................... 10 2009 027 165

(51) Int. Cl.
| | |
|---|---|
| *G06F 15/18* | (2006.01) |
| *G06E 1/00* | (2006.01) |
| *G06E 3/00* | (2006.01) |
| *G06G 7/00* | (2006.01) |
| *G06N 3/02* | (2006.01) |

(52) U.S. Cl.
USPC ........................................................ 706/15

(58) Field of Classification Search
USPC ........................................................ 706/15
See application file for complete search history.

(56) References Cited

U.S. PATENT DOCUMENTS 8,422,768 B2 *   4/2013   Raymond et al. ............. 382/156

OTHER PUBLICATIONS

Guo et al., "Wavefront reconstruction with artificial neural networks," XP-002606609, vol. 14, No. 14, pp. 6456-6462, 2006.*
Guo et al., "Wavefront reconstruction with artificial neural networks," XP-002606609, vol. 14, No. 14, pp. 6456-6462, Jul. 10, 2006, Optics Express.
"V1KU Image recognition module," *General Vision*, XP-002606610, Mar. 2009, http://www.general-vision.com/Datasheet/DS_V1KU.pdf.
Qi et al., "Wavefront fitting of interferograms with Zernike polynomials," *Society of Photo-Optical Instrumental Engineers*, XP-002606611, vol. 41, No. 7, pp. 1565-1569, Jul. 2002.
International Search Report dated Nov. 18, 2010 in International Patent Application No. PCT/IB2010/001545 (with translation).

* cited by examiner

*Primary Examiner* — Michael B Holmes
(74) *Attorney, Agent, or Firm* — Oliff & Berridge, PLC

(57) ABSTRACT

The invention concerns a process for the representation of a scanning function by means of a neuronal network and a device for the implementation of the process, whereby measurement values associated with a turbulent wave front, which contain phase information, are compared with reference values, with the result that the intermediate values thus obtained can be compared with comparison functions, in order, in the best case, to describe the measured pattern with a selection of comparison functions, whereby a neuronal network is trained in the comparison functions, so that the processing of the measured pattern can take place in near-real time.

17 Claims, 3 Drawing Sheets

PROCESS AND DEVICE FOR REPRESENTATION OF A SCANNING FUNCTION

Figure 1:
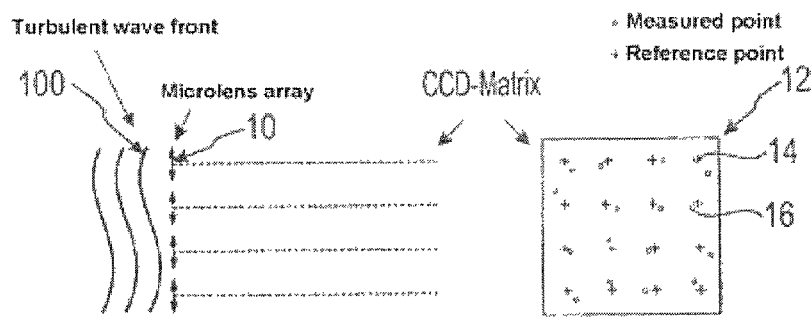

The present invention concerns a process for the representation of a scanning function by means of a neuronal network in accordance with claim 1 and a device for the implementation of the process in accordance with claim 11. A data carrier medium with an appropriate program which corresponds to the process according to the invention is claimed in claim 17.

If a scanning beam is transmitted and its response is analyzed, there are various interfering influences which can make the analysis and evaluation of the response difficult or even impossible. Especially when laser technology is used, the beam quality and the ability to focus the laser beam play an important role. In addition, a high optical resolution of the response of a laser beam has a considerable effect on the result of a scan.

If a laser beam is transmitted and its response is recorded as set forth above, a turbulent wave front, which may represent a scanning function, encounters a preferably at least two dimensional array of optical elements, such as lenses, diffraction gratings and the like, which enable the conversion of the incident scanning function into component parts which contain phase information. The component parts of the scanning function, which, for example, are broken down by a microlens array, encounter a measuring sensor with a two dimensional structure of measuring elements. This type of sensor may, for example, consist of a CCD sensor matrix.

In the case of a planar wave front—that is, a phase or wave front which is perpendicular to the direction of the beam propagation, the microlens array would break down the incident wave front in such a way that reference points on the CCD matrix, which are preferably equidistant, would be encountered. However, because the incident wave front, as the response of a coherent laser beam, is a turbulent wave front with considerable phase interference, the lenses of the microlens array, which, in principle, are to be considered as a grid, will generate mapping points on the CCD matrix, which are deflected relative to the reference points.

Typically, the displacement of the measured points relative to the reference positions, which constitute a measurement of the slope of the local phase front, is determined by integration of the real phase front. In this context, only an absolute offset is to be taken into account. A further process generates an interference pattern which is associated with the phase function and distributed over the entire image of the CCD matrix; the slope of the local phase front can similarly be calculated on the basis of that interference pattern.

The process as set forth above, however, take a great deal of time, so that correction in real time or near-real time can only be accomplished in the simplest of cases. In realistic cases, which are regularly encountered in, for example, applications in ophthalmology, pattern recognition in navigation, or military fields, correction of this type is not possible. Accordingly, in such cases, images must be buffered and evaluation of the images must take place in the subsequent stage.

In light of that set forth above, an objective of the present invention is to create at least partial corrective measures in order to overcome at least some of the advantages of the state of the art. It should especially be possible to undertake the phase corrections in question in near-real time even in complex cases.

The advantages which may be achieved according to the invention are based on a process and a device according to the respective independent claim. Advantageous embodiments of the objects according to the invention are defined in the dependent claims.

For the representation of a scanning function by means of a neuronal network, the scanning function is first optically broken down into parts which contain phase information. Subsequently, the component parts which contain the phase information are transmitted to the neuronal network for processing. The neuronal network has access to a plurality of comparison functions and/or is trained in those comparison functions. Through comparison of the fate of information with one or more of the comparison functions, a primary comparison function is selected, whereby a pre-determinable deviation or a deviation extremum serves as a criterion for the selection. To select the primary comparison function is determined as a representation function, and preferably as the dominant representation function.

A device which can also be used for the performance of the process according to the invention includes an at least two-dimensional array of receivers with a plurality of preferably optical sensors and/or detectors distributed thereon. An at least two-dimensional array of optical elements, such as lenses, diffraction gratings and the like, which converts the incident scanning function into component parts which contain phase information, is provided before the receiver array—for example, a CCD sensor matrix. The component parts which contain phase-relevant information, which come from the receiver array, are entered into the neuronal network. The neuronal network has access to a storage unit with a plurality of comparison functions and/or is trained in those functions. In this way, the neuronal network can compare the component parts of the scanning functions with at least one of the comparison functions, can select at least one of the comparison functions as a preferably dominant comparison function, and can describe the scanning function therewith.

In this connection, it is quite possible that the primary comparison functions originate in a complete function base and/or represent at least one subset of the functions of such a function base. These functions form a set of interferometry patterns which, in a turbulent wave front which is to be measured, are again to be found as phase distribution functions. The neuronal network receives, as input information, the component parts and/or input vectors of the displacement vectors of all points in the scanning functions and can process them in parallel. The network can now recognize the functions from the complete function base, in which the neuronal network is trained and/or to which it has access, and the amplitude of those functions, in the scanning function. It accordingly becomes possible to mathematically reconstruct the turbulent wave front which has been measured and is accessible as a scanning function, by means of the recognized base functions of a complete function base. As an example of a usable neuronal network, a network of the "CogniMem" type, which is available from the company known as General Vision, USA, may be used.

Figure 2:
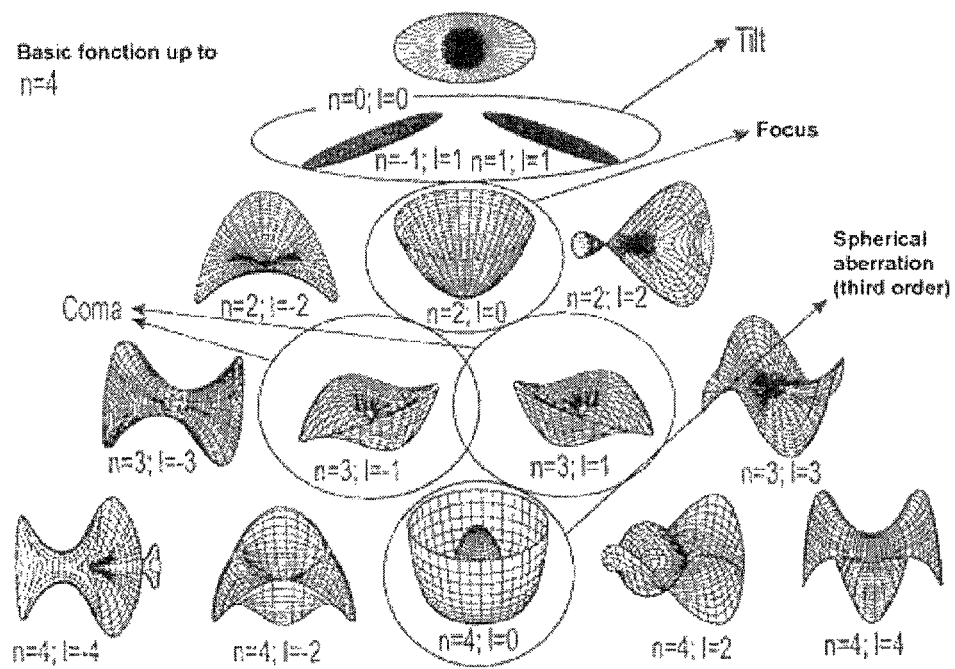
Figure 3:
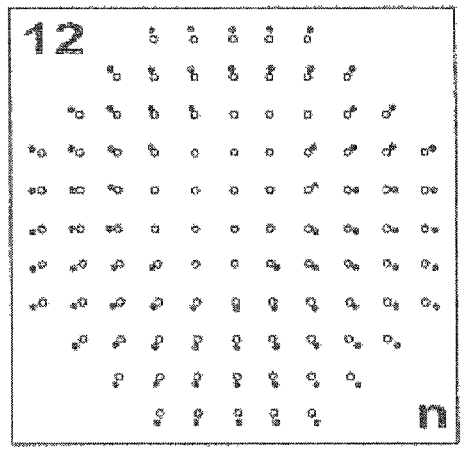
Figure 4:
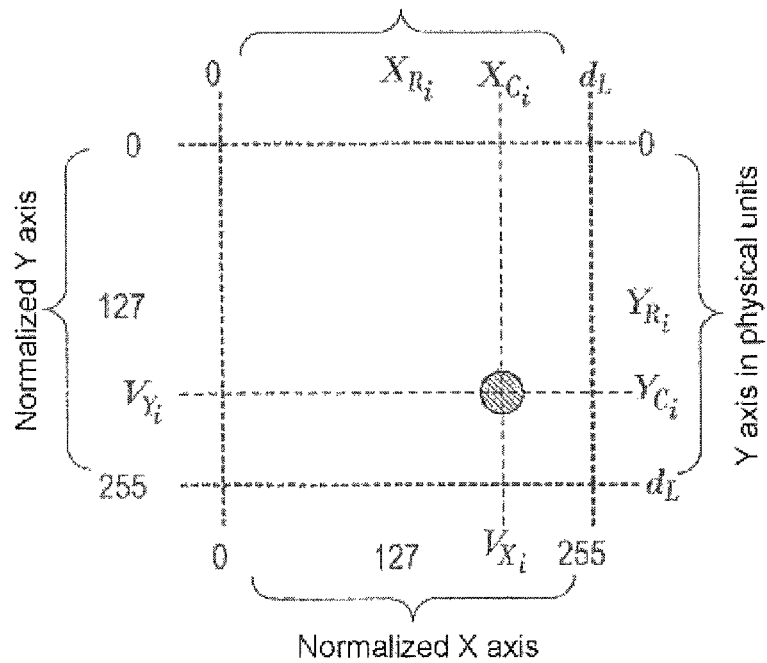
Figure 5:
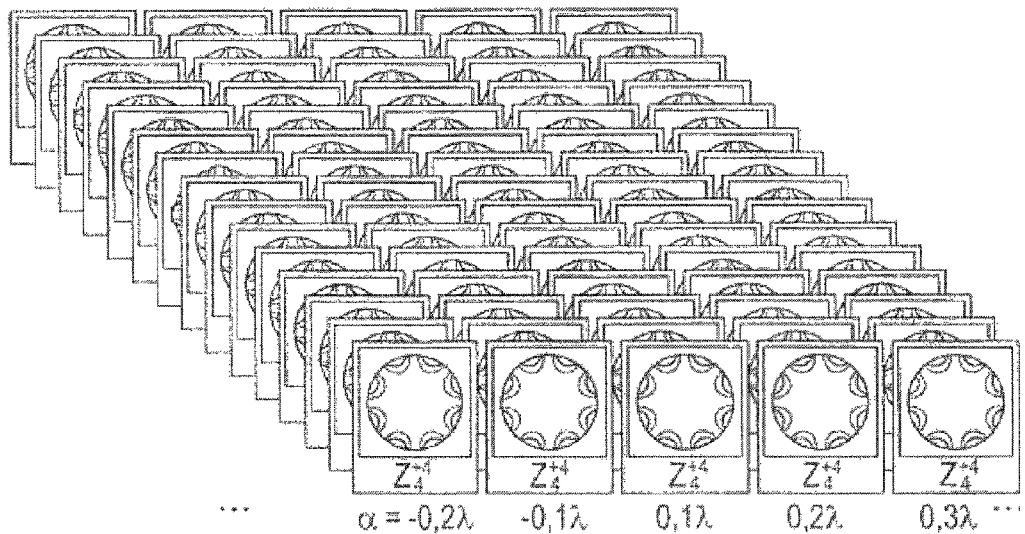
Figure 6:
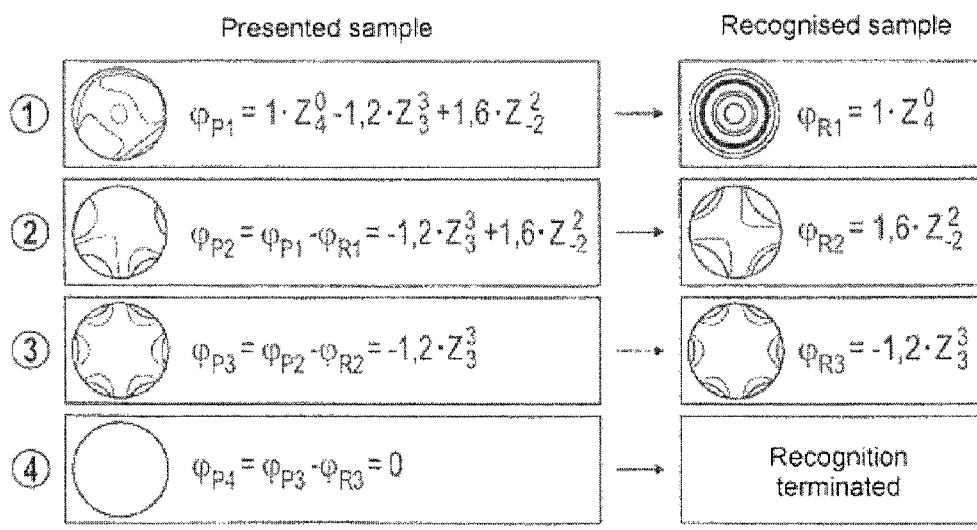

A preferred embodiment according to the invention is described in greater detail below, with reference to the figures attached hereto. This includes a description of additional features and advantages according to the invention, which, either singly or in combination, may become the objects of claims. The figures show:

FIG. 1: a representation in principle of a measuring array which may be used according to the invention;

FIG. 2: several functions, in this case Zernike polynomials, and the aberrations associated therewith;

FIG. 3: an example of a recorded point pattern of the scanning function, relative to reference points of an ideal response;

FIG. 4: a normalization of displacements of measured points relative to reference points into 8-bit values;

FIG. 5: a selection of comparison functions for the comparison of the scanning function with the comparison functions from a neuronal pattern database and/or for a neuronal network; and FIG. 6: an example in principle of a flow chart for the representation of the scanning function by means of comparison functions recognized in the scanning function.

FIG. 1 indicates an arrangement in principle of the detector. What is shown is a Shack-Hartmann sensor (SHS) which is encountered by a turbulent wave front 100. The wave front encounters a two-dimensional microlens array which breaks the wave front down into different maxima, which are generated by the respective lenses. A non-turbulent wave front would allow a pattern to form on a two-dimensional detector, such as a CCD sensor matrix, which has an ideal construction, whereby equidistant mappings would arise on the CCD sensor matrix by means of the various microlenses.

Accordingly, in the ideal case, mapping points 14 form on the CCD sensor matrix 12, insofar as the incident wave front is planar and encounters the lens array vertically. Insofar as the wave front is a turbulent wave front 100, the incoherent component parts of the wave front will lead to an offset of the mapping points of the microlenses in the microlens array 10 and thereby to mapping points 16 on the CCD sensor matrix 12. The offset between the mapping points 16 and the reference points 14 corresponds to the slope of the local phase front. Aside from the Shack-Hartmann process, quadri-wave lateral shearing interferometry may also be considered for the purposes of the invention.

The measured phase distribution must then be analyzed and mathematically broken down into comparison functions of a complete function basis.

FIG. 2, by way of example, represents several Zernike polynomials, with which an unequivocal breakdown of a measured phase distribution of a wave front may be performed.

According to the invention, a set of comparison functions is made available to a neuronal network and/or the neuronal network is trained in the set of comparison functions. These constitute a subset of functions of a complete function base and, in the case of FIG. 2, of the Zernike polynomials. The neuronal network is employed with displacement vectors of all points, which serve as input sectors [sic; should be "input vectors"]. On the basis of the structure of neuronal networks, these information items can be processed in parallel. An advantage of the process according to the invention lies in the fact that the use of a large number of reference points and/or measured points, thanks to the special network, does not give rise to an extension of the processing time. In addition, increasing the number of reference and/or measuring points leads to a better resolution.

In order to be able to perform the recognition of comparison functions within the scanning function, it is necessary to first convert a recorded pattern with measuring points—for example, so the calculation of the center of gravity—into matrices. In this way, for the camera cell associated with one lens of the microlens array, two matrices, $X_C$ and $Y_C$, which contain the X and Y positions of the points, are first calculated. In the example set forth below, the positions are also shown in Equation (1) in meters.

$$X_C = \begin{bmatrix} X_{C_1} & X_{C_2} & \ldots & \ldots \\ \ldots & \ldots & \ldots & \ldots \\ \ldots & X_{C_1} & \ldots & \ldots \\ \ldots & \ldots & \ldots & X_{C_2} \end{bmatrix} \quad Y_C = \begin{bmatrix} Y_{C_1} & Y_{C_2} & \ldots & \ldots \\ \ldots & \ldots & \ldots & \ldots \\ \ldots & Y_{C_1} & \ldots & \ldots \\ \ldots & \ldots & \ldots & Y_{C_2} \end{bmatrix} \quad (1)$$

Two reference matrices, $X_R$ and $Y_R$ according to Equation (2), describe the midpoints of the positions associated with each lens on the CCD sensor matrix.

$$X_R = \begin{bmatrix} X_{R_1} & X_{R_2} & \ldots & \ldots \\ \ldots & \ldots & \ldots & \ldots \\ \ldots & X_{R_1} & \ldots & \ldots \\ \ldots & \ldots & \ldots & X_{R_2} \end{bmatrix} \quad Y_R = \begin{bmatrix} Y_{R_1} & Y_{R_2} & \ldots & \ldots \\ \ldots & \ldots & \ldots & \ldots \\ \ldots & Y_{R_1} & \ldots & \ldots \\ \ldots & \ldots & \ldots & Y_{R_2} \end{bmatrix} \quad (2)$$

The point pattern shown in FIG. 3, with the reference points on one side and the points of the scanning pattern on the other side, represent an example which may also be derived, for example, from FIG. 1. Thereby, the coordinates $(X_{Ci}, Y_{Ci})$ result for the pattern components represented as points which represent measurement values. The points which are made visible in the form of crosses refer to the reference values, onto which the measurement values should have been directly projected, if the incident wave front were not turbulent. These reference values shall be designated as $(X_{Ri}, Y_{Ri})$ below, where I=1 ... n and n corresponds to the number of lenses in the array.

The following example illustrates the neuronal algorithm by means of the presently available and/or usable CogniMem technology, which is capable of classifying input vectors a maximum of 256 bytes (8-bit words) long. The process according to the invention is not limited to this technology. Based on the predetermined measurement and reference matrices, and taking into account the lens width/length dL in meters, the input vector of the neuronal network corresponding to the point pattern is calculated as follows (Equations (3), (3.1) and (3.2)):

$$V = (V_{X_1} \quad V_{Y_2} \quad \ldots \quad \ldots \quad V_{X_n} \quad V_{Y_n}) \quad (3)$$

$$V_{X_1} = \left\lfloor \frac{\left(X_{C_1} - X_{R_1} + \frac{d_L}{2}\right)}{d_L} \cdot 255 \right\rfloor \quad (3.1)$$

$$V_{Y_1} = \left\lfloor \frac{\left(Y_{C_1} - Y_{R_1} + \frac{d_L}{2}\right)}{d_L} \cdot 255 \right\rfloor \quad (3.2)$$

Accordingly, all of the reference points $(X_{Ri}, Y_{Ri})$ are mapped on the point (127, 127).

The measurement points $(X_{Ci}, Y_{Ci})$ are mapped within the lens cell in the range between 0 and 255 (see also FIG. 3).

The length of the input vector $L_V$ is calculated from the number of lenses $n_{Lx}$ and $n_{Ly}$ (in the X and Y directions respectively) which are used for mapping the phase front (Equation (4)).

$$L_V = 2 \cdot n_{Lx} \cdot n_{Ly} \quad (4)$$

The maximum length of 256 bytes, in this example, as may be seen from FIG. 4, must not be exceeded. Accordingly, as shown in FIG. 4, only 11×11 lenses are used for reconstruction of the phase front. As a result, the corresponding input vector therefore has a length of 242 bytes.

Vectors constructed in this forum can now be transmitted to the neuronal network, both as a pattern for training and for recognition. In the following equations, the transformation of phase distributions into the relevant input vectors is described as follows:

$$V = \Psi(\phi) \tag{5}$$

In equation (5), V stands for the resulting input vector which arises from the original phase distribution $\phi$ through the use of the Shack-Hartmann procedure, as well as the performance of the transformations described in Equations (3), (3.1) and (3.2).

The described transformation is thereby reversible: that is, if the physical data used for the transformation (links, etc.) are known, it is always possible to reproduce the relevant phase distribution $\phi$ from a known input vector V. This retransformation $\Psi'$ is described in Equation (6):

$$\phi = \Psi'(V) \tag{6}$$

In order to be able to use the neuronal network for the classification of phase fronts, it is necessary, at the time of conception of the systems, to create a database with known basic phase distributions, which correspond to specific optical interferences, and to train the neuronal network in them.

Usable for this purpose, for example, are the aforementioned Zernike polynomials, to which a direct physical meaning can be assigned. According to the measuring task, a selection of desired polynomials is generated and a range and step width for the discretization of the amplitude of the vast described phase interference are determined. The relevant phase distributions can then be determined by calculation and, after conversion into input vectors, the neuronal network can be trained in them. FIG. 5 is a graphic representation of a sample extract of a neuronal database created in this way; the example consists of the first 15 Zernike polynomials (up to and including the fourth order) with an amplitude discretization of $0.1\lambda$.

The accuracy of the recognition results provided by the neuronal network depends on the range determined and the disintegration of the amplitude, as well as on the number of learned basic polynomials. This naturally means that the pattern database will vary in size accordingly.

Classic, sequential algorithms require more calculation time with each data record, in order to allocate a presented pattern. This allows real-time applications to only a limited degree and, in many cases only by means of high-performance, expensive processors.

The CogniMem technology used in the example described in this document allows the classification of input patterns with a constant calculation time (approximately 10 µs per pattern), irrespective of the size of the database (number of occupied neurons) and at an attractive price (approximately € 60 per chip).

If the neuronal network is presented with a Zernike polynomial encoded according to the method set forth above, it will automatically answer, following a recognition time interval, with the category (data record number) of the pre-trained polynomial which fits it best. This also works when the network is presented with modified polynomials—that is, for example, known polynomials with an amplitude which does not appear in the database. The invention uses this capability in order to generalize unknown input polynomials into a known pattern. This is important in order to be able to break down a measured phase distribution into its corresponding linear combination of Zernike polynomials. For the best possible results, that is, with the least error, this is done on the basis of a pre-trained database.

To this end, a very simple, iterative algorithm is used, which requires relatively very little calculation time.

Preferably, for the variant procedure explained above, an input vector generated according to that set forth above (see Equations (3), (3.1) and (3.2)) is used, which describes a phase distribution composed of any desired number of linear combinations of Zernike polynomials in which the network has been previously trained. The following equation describes this by means of an example:

$$V_{P1} = \Psi(\varphi_{P1} = 1 \cdot Z_4^0 - 1{,}2 \cdot Z_3^3 + 1{,}6 \cdot Z_{-2}^2) \tag{7}$$
$$= (VP1_{X_1} \quad VP1_{Y_2} \quad \ldots \quad \ldots \quad VP1_{X_n} \quad VP1_{Y_n})$$

In equation (5) [sic; should be (7)], $V_{P1}$ is the input vector which results for the phase distribution in the example, $\phi_1$, which can include the elements $VP1_{X_1}$ through $VP1_{Y_n}$.

This vector is now presented to a neuronal network, for example, a CogniMem chip, which was previously trained according to FIG. 4, for recognition. After the expiry of an interval required for the recognition, the neuronal network gives back the pattern which best fits the presented vector (Equation (8)):

$$\phi_{R1} = \Psi'(VR1_{X_1} VR1_{Y_2} \ldots VR1_{X_n} VR1_{Y_n}) = 1 \cdot Z_4^0 \tag{8}$$

In the polynomial in the example, $\phi_{P1}$, $\phi_{R1}$ represents the most dominant contribution. Because $\phi_{P1}$ is a linear combination of the polynomials known to the neuronal network, the difference between $\phi_{P1}$ and $\phi_{R1}$ will similarly be a linear combination of known polynomials. The difference is converted into an input vector. This vector, in a second recognition step, is again evaluated and can also be transmitted, for example, to the CogniMem chip for evaluation (Equation (9)).

$$V_{P2} = \Psi(\varphi_{P2} = \varphi_{P1} - \varphi_{R1} = -1{,}2 \cdot Z_3^3 + 1{,}6 \cdot Z_{-2}^2) \tag{9}$$
$$= (VP2_{X_1} \quad VP2_{Y_2} \quad \ldots \quad \ldots \quad VP2_{X_n} \quad VP2_{Y_n})$$

As in the previous recognition step (Equation 8)), the neuronal network will again find the most dominant known Zernike polynomial as a contribution contained in the vector $V_{P2}$:

$$\phi_{R2} = \Psi'(VR2_{X_1} VR2_{Y_2} \ldots VR2_{X_n} VR2_{Y_n}) = 1{,}6 \cdot Z_{-2}^2 \tag{10}$$

Now, similarly to Equation (9), the difference between the presented polynomial $\phi_{P2}$ and $\phi_{R2}$ will be calculated and again presented to the neuronal network (Equation (11)):

$$V_{P3} = \Psi(\varphi_{P3} = \varphi_{P2} - \varphi_{R2} = -1{,}2 \cdot Z_3^3) \tag{11}$$
$$= (VP3_{X_1} \quad VP3_{Y_2} \quad \ldots \quad \ldots \quad VP3_{X_n} \quad VP3_{Y_n})$$

The new input vector $V_{P3}$ will again be transmitted to the network for recognition, and the result (Equation (12)) is unequivocal:

$$\phi_{R3} = \Psi'(VR3_{X_1} VR3_{Y_2} \ldots VR3_{X_n} VR3_{Y_n}) = -1{,}2 \cdot Z_{-3}^3 \tag{12}$$

The described steps in the variant of the process according to the invention: a) recognition of the dominant pattern, b) calculation of the difference and c) presentation of the new pattern, will be repeated until "0" is achieved for the presented difference pattern (Equations (13.1), (13.2)), or until another definable end criterion (for example, maximum number of summands in the linear combination) is achieved.

$$\phi_{Pk} = \phi_{P(k-1)} - \phi_{R(k-1)} = 0 \quad (13.1)$$

$$\phi_{Rk} = 0 \quad (13.2)$$

In our example, the recognition ended after the third step. The fourth vector presented to the network, $V_{P4}$, is recognized as "0" (Equation (14)):

$$V_{P4} = \Psi(\varphi_{P4} = \varphi_{P3} - \varphi_{R3} = 0) \quad (14)$$
$$= (VP4_{X_1} \quad VP4_{Y_2} \quad \ldots \quad \ldots \quad VP4_{X_n} \quad VP4_{Y_n})$$

The sum of the recognized individual polynomials $\phi_{R1} \ldots \phi_{Rn}$ then gives the original linear combination $\phi_{P1}$ (Equation (15)):

$$\varphi_{R(Total)} = \sum_{l=1}^{n} \varphi_{R1} = \varphi_{P1} \quad (15)$$

The neuronal network, thanks to its capability for generalization, is accordingly capable of breaking down a given function into linear combinations of nonlinear independent functions, such as Zernike polynomials, which may be represented as a valid input vector, in only a few steps. FIG. 6 provides a graphic illustration of the operations carried out in the example.

Should one of the recognition steps described above, in practice, not immediately give back the most dominant polynomial component (or not in the correct amplitude), this does not constitute a fault. Because the algorithm always attempts to bring the difference of the phase distribution as close to "0" as possible, any deviation will be automatically corrected in one of the subsequent recognition steps.

In the example, a combination which consists of known components was presented to the network. Thanks to the network's capacity for generalization, the question: "What happens when one or more components of the linear combination are not known to the network?" may be answered as follows: "The next best known function will then be selected." Admittedly, the error calculation as shown in Equation (15) will then show a corresponding error. This error, however, will be automatically minimized as far as possible by the neuronal network.

This behavior of the neuronal network may even be exploited for its application. Accordingly, for example, certain Zernike polynomials represent specific optical properties—such as tilt, focus or spherical aberrations. In order to reduce the size of the database and thereby also the number of necessary recognition steps, it is possible to put in a spatial filter, such as a Fourier optical telescope array, before the SHS. This will mean that only the lower order polynomials are allowed to pass through and are converted into data by the SHS. If the neuronal network is accordingly trained on "only" one database of these specific Zernike polynomials with physical relevance to specific aberrations, the system will attempt to represent the presented measurements in the best possible way. The result thus obtained may then be interpreted as a minimized-error measurement of the optical properties previously defined by training.

The recognition time for a complete linear combination depends on the number of participating components which are known to the neuronal network. For the example set forth above, the net recognition time through the use of a CogniMem chip will be approximately 40 μs, because four recognition steps were necessary. The calculation time for the formation of the differences is, of course, added to this time. Given the linear nature of the differentiation, this difference formation can be directly performed with the input vectors, without having to re-transform the real phase functions. This can be simply solved with integer arithmetic and can easily be performed on hardware (such as FPGA).

The invention described above, thanks to its high processing speed, is especially suitable for real-time measurement of the properties of optical systems in the kHz range and further.

The process described above can also easily be transferred to the decomposition of other linear combinations of a set of known linear independent basic functions. Accordingly, the process is, generally speaking, applicable to any measurement or recognition problem in which a function of one or more variables is to be broken down mathematically into linear independent basic functions. The process is similarly independent of the technology of the neuronal network, because it only uses the properties of the neuronal network for recognition, classification and generalization. It does not matter how these properties are actually realized in hardware or software.

The invention claimed is:

1. A process for the representation of a scanning function by means of a neuronal network, with the following steps:
   transmitting the scanning function to the neuronal network for processing;
   making available a number of comparison functions to the neuronal network;
   comparing the scanning function with one or more of the comparison functions;
   selecting a primary comparison function whereby a pre-determinable deviation or a deviation extremum serves as a criterion for the selection; and
   determining the selected primary comparison function as a representation function,
   wherein, if a deviation or a deviation extremum which is larger than a pre-determinable value is determined, the representation function is subtracted from the scanning function and a difference is processed like the original scanning function.

2. The process according to claim 1, wherein a difference function is formed until a result falls below the pre-determinable value or until another end criterion is reached.

3. The process according to claim 1, wherein determined representation functions, in their entirety, represent the scanning function.

4. The process according to claim 1, wherein the neuronal network has as narrow as possible, a successive step width for a discretization of an amplitude of the representation function, and/or a broad range for representation functions and/or as large a number as possible of learned representation functions.

5. The process according to claim 1, wherein functions from a complete function base, are used as representation functions.

6. The process according to claim 1, wherein the scanning function corresponds to an input sample, which is transmitted to the neuronal network for recognition of representation functions contained therein.

7. The process according to claim 1, wherein a transmitter is used and a response to the transmitter radiation disperses at least two-dimensionally, whereby two-dimensionally distributed sensors or detectors convert the response radiation into an input pattern.

8. The process according to claim 1, wherein a phase front of a turbulent wave front of optical radiation is used as an input pattern.

9. The process according to claim 8, wherein optical pre-filtering according to spatial frequencies is performed, so that the input pattern is simplified.

10. The process according to claim 1, wherein a sample pattern which represents the scanning function is brought to the neuronal network in the form of an input vector, and the comparison functions of the network are accessible in the form of vectors in order to perform the representation.

11. The process according to claim 1, wherein the difference is converted into an input vector and transmitted to the neuronal network for further representation.

12. A device for the representation of a scanning function by means of a neuronal network, comprising:
   an at least two-dimensional array of receivers with a plurality of sensors and/or detectors distributed thereon;
   an at least two-dimensional array of optical elements, such as lenses, which converts the incident scanning function into component parts which contain phase information;
   a neuronal network in which component parts which come from the receiver array are entered; and
   whereby the neuronal network has access to a plurality of comparison functions, in order to describe the component parts of the scanning function with at least one of the comparison functions.

13. The device according to claim 12, wherein an optical pre-filtering facility is provided, which subjects the scanning function to pre-filtering according to spatial frequencies.

14. The device according to claim 12, wherein at least one transmitter is provided for a generation of radiation.

15. The device according to claim 12, wherein an arrangement of the at least two-dimensional receiver array includes a Shack-Hartmann sensor or a quadri-wave lateral shearing interferometry sensor.

16. The device according to claim 12, wherein the at least two-dimensional receiver array and the at least two-dimensional array of optical elements, which form a phase front detector, and the neuronal network form a single functional unit, which, as measuring data, outputs only the coefficients of the base development.

17. The device according to claim 12, wherein the device is, in addition, configured in such a way as to enable performance of the process according to claim 1.

* * * * *